US00PP23468P2

(12) United States Plant Patent
Koppe

(10) Patent No.: US PP23,468 P2
(45) Date of Patent: Mar. 12, 2013

(54) ***BEGONIA* PLANT NAMED 'KRBELIF01'**

(50) Latin Name: *Begonia hybrida*
Varietal Denomination: KRBELIF01

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 13/065,261

(22) Filed: Mar. 17, 2011

(51) Int. Cl.
*A01H 5/00* (2006.01)
(52) U.S. Cl. ..... Plt./343
(58) Field of Classification Search ..... Plt./343
See application file for complete search history.

*Primary Examiner* — Annette Para
(74) *Attorney, Agent, or Firm* — C. A. Whealy

(57) ABSTRACT

A new and distinct cultivar of *Begonia* plant named 'KRBELIF01', characterized by its upright, outwardly spreading and mounded plant habit; freely branching habit; dark greyed purple-colored leaves; and excellent postproduction longevity.

2 Drawing Sheets

Botanical designation: *Begonia hybrida.*
Cultivar denomination: 'KRBELIF01'.

BACKGROUND OF THE INVENTION

The present invention relates to a new and distinct cultivar of *Begonia* plant, botanically known as *Begonia hybrida* and hereinafter referred to by the name 'KRBELIF01'.

The new *Begonia* plant is a naturally-occurring whole plant mutation of *Begonia hybrida* 'Inca Fire', not patented. The new *Begonia* plant was discovered and selected by the Inventor as a single plant within a population of plants of 'Inca Fire' in a controlled greenhouse environment in Ermelo, The Netherlands in August, 2006.

Asexual reproduction of the new *Begonia* plant by leaf cuttings in a controlled greenhouse environment in Ermelo, The Netherlands since November, 2006, has shown that the unique features of this new *Begonia* plant are stable and reproduced true to type in successive generations.

SUMMARY OF THE INVENTION

Plants of the new *Begonia* have not been observed under all possible environmental conditions and cultural conditions. The phenotype may vary somewhat with variations in environmental conditions such as temperature, daylength and light intensity, without, however, any variance in genotype.

The following traits have been repeatedly observed and are determined to be the unique characteristics of 'KRBELIF01'. These characteristics in combination distinguish 'KRBELIF01' as a new and distinct *Begonia* plant:

1. Upright, outwardly spreading and mounded plant habit.
2. Freely branching habit.
3. Dark greyed purple-colored leaves.
4. Excellent postproduction longevity.

Plants of the new *Begonia* differ primarily from plants of the parent, 'Inca Fire', in leaf color as plants of 'Inca Fire' have lighter-colored leaves than plants of the new *Begonia.*

Plants of the new *Begonia* can be compared to plants of *Begonia Hybrida* 'Indian Summer', not patented. In side-by-side comparisons conducted in Ermelo, The Netherlands, plants of the new *Begonia* differed primarily from plants of 'Indian Summer' in leaf color as plants of 'Indian Summer' had lighter-colored leaves.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRBELIF01' grown in a container.

The photograph on the second sheet is a close up view of the upper and lower surfaces of typical leaves of 'KRBELIF01'.

DETAILED BOTANICAL DESCRIPTION

The aforementioned photographs and following observations and measurements describe plants grown during the winter in 13-cm containers in a glass-covered greenhouse in Ermelo, The Netherlands, under commercial cultural practices. During the production of the plants, the average day temperature was 20° C. and the average night temperature was 18° C. Plants were eight weeks old when the photographs and description were taken. In the following description, color references are made to The Royal Horticultural Society Colour Chart, 2007 Edition, except where general terms of ordinary dictionary significance are used.

Botanical classification: *Begonia hybrida* 'KRBELIF01'.

Parentage: Naturally-occurring whole plant mutation of *Begonia hybrida* 'Inca Fire', not patented.

Propagation:

*Type.*—By leaf cuttings.

*Time to develop roots.*—About 20 days at temperatures of 20° C.

*Time to produce a rooted young plant.*—About five weeks at temperatures of 20° C.

*Root description*.—Fine, fibrous; white to orange brown in color.

*Rooting habit*.—Freely branching; medium density; plants of the new *Begonia* have not been observed to form tubers.

Plant description:

*Plant and growth habit*.—Upright, outwardly spreading and mounded plant habit, flattened globular in shape; freely branching habit with about nine basal branches developing per plant; moderately vigorous growth habit.

*Postproduction longevity*.—Plants maintain good leaf substance for at least 70 days under interior landscape conditions.

*Plant height*.—About 20 cm.

*Plant width*.—About 38.3 cm.

*Lateral branches*.—Length: About 1.6 cm. Diameter: About 1.4 cm. Internode length: About 3 mm. Texture: Slightly rough; glabrous. Color: Close to N186C tinged with close to 200A.

*Leaves*.—Arrangement: Alternate; simple. Length: About 14 cm. Width: About 9.3 cm. Shape: Ovate. Apex: Acuminate to slightly apiculate. Base: Oblique. Margin: Shallowly lobed. Texture, upper and lower surfaces: Smooth, glabrous; velvety. Venation pattern: Palmate. Color: Developing leaves, upper surface: Close to 59B and 187D. Developing leaves, lower surface: Close to 187C. Fully expanded leaves, upper surface: Close to 187C; venation, close to N186C. Fully expanded leaves, lower surface: Close to 187A strongly tinged with close to N187B to N187C; venation, close to N186C. Petioles: Length: About 12.6 cm. Diameter: About 4 mm. Texture, upper and lower surfaces: Sparsely pubescent. Color, upper and lower surfaces: Close to N186C.

Flower description: Flower development has not been observed on plants of the new *Begonia*. The new *Begonia* was selected on the basis of its unique foliage characteristics and its lack of flowers.

Postproduction longevity: Plants last about six weeks under interior conditions.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'KRBELIF01' as illustrated and described.

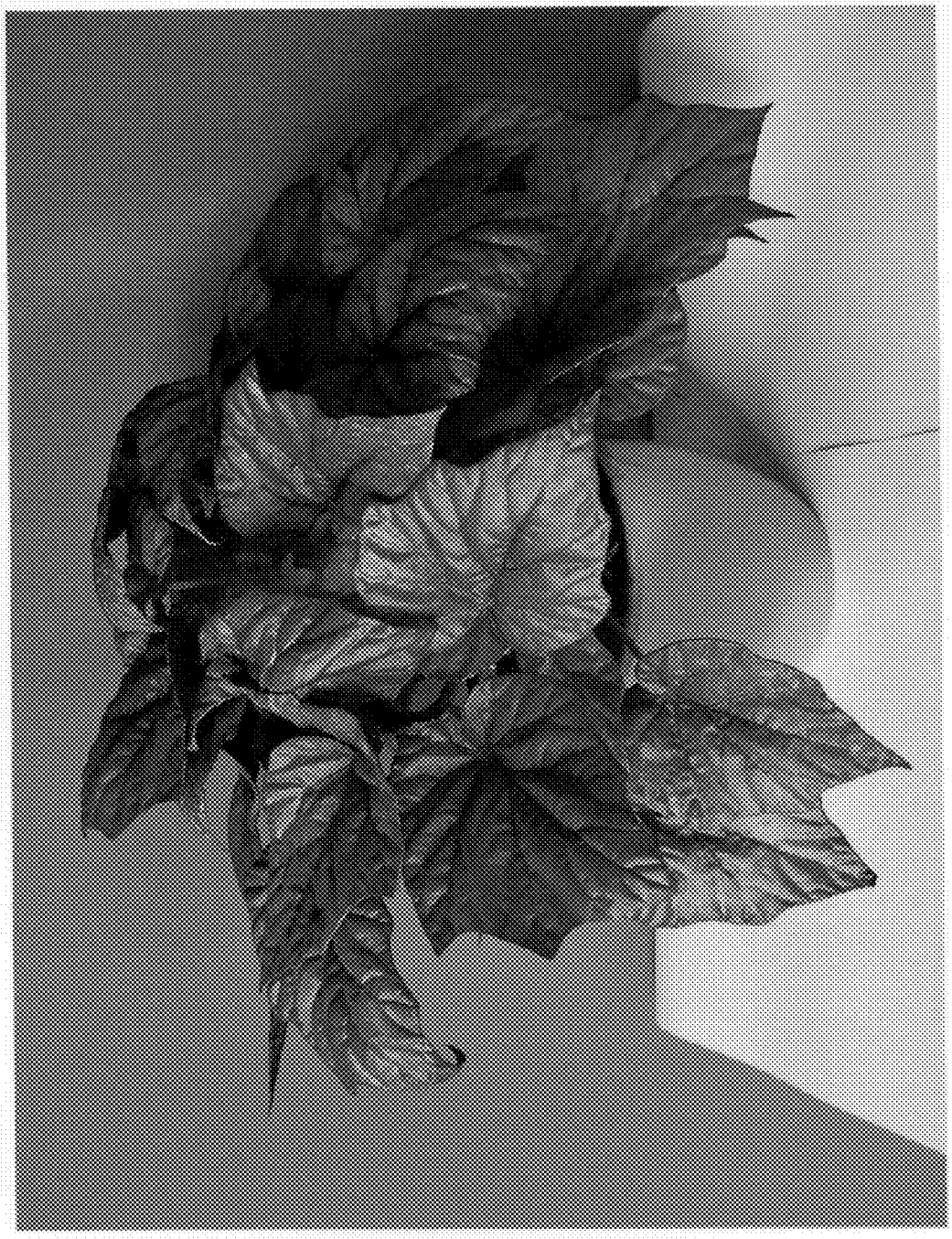

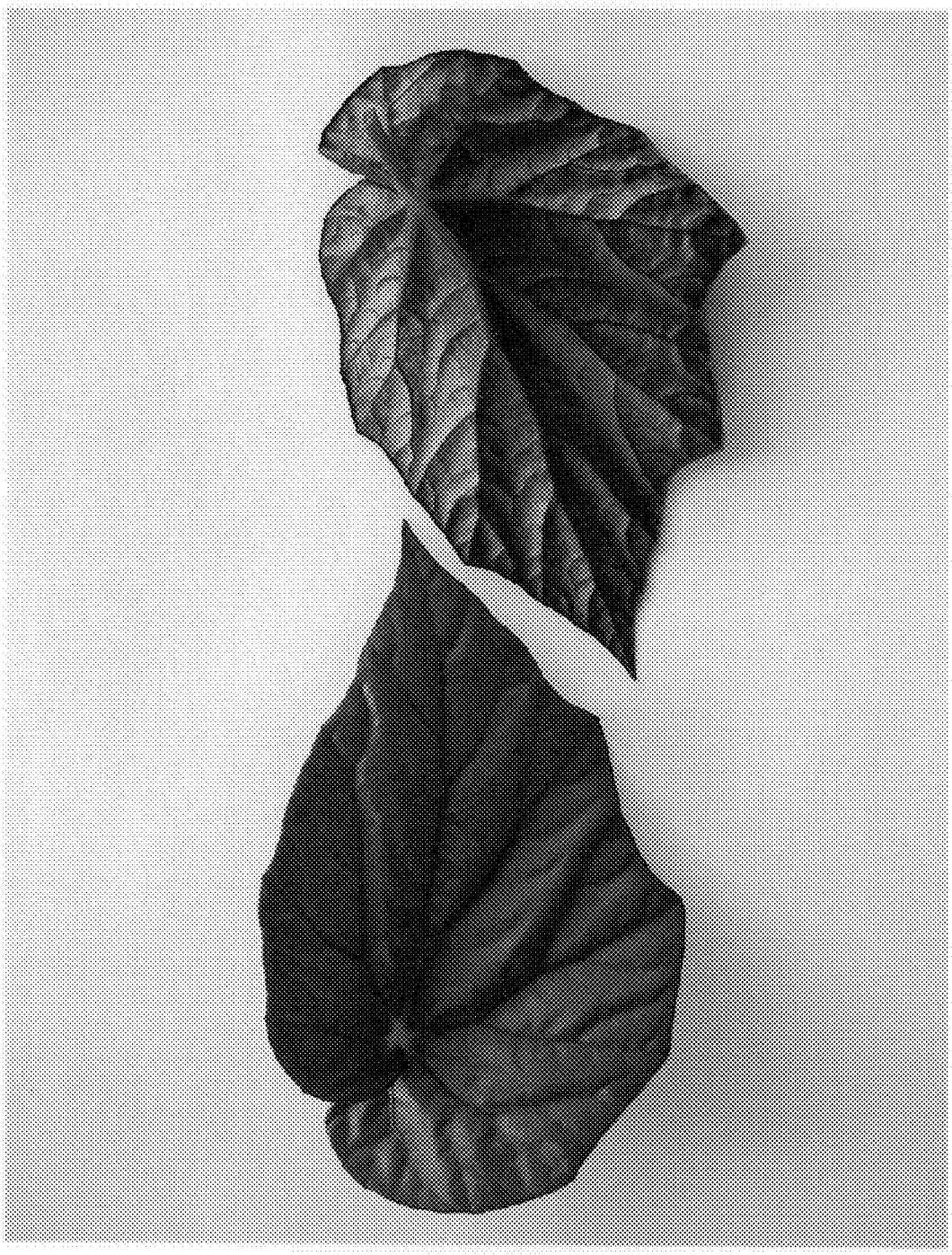

* * * * *